United States Patent
Zhu

(10) Patent No.: US 10,132,302 B2
(45) Date of Patent: Nov. 20, 2018

(54) INFUSION PUMP INCLUDING REVERSE LOADING PROTECTION

(71) Applicants: Baxter International Inc., Deerfield, IL (US); Baxter Healthcare S.A., Glattpark (Opfikon) (CH)

(72) Inventor: Hong Zhu, Buffalo Grove, IL (US)

(73) Assignees: BAXTER INTERNATIONAL INC., Deerfield, IL (US); BAXTER HEALTHCARE S.A., Glattpark (Opfikon) (CH)

(*) Notice: Subject to any disclaimer, the term of this patent is extended or adjusted under 35 U.S.C. 154(b) by 710 days.

(21) Appl. No.: 13/947,193

(22) Filed: Jul. 22, 2013

(65) Prior Publication Data

US 2015/0023808 A1     Jan. 22, 2015

(51) Int. Cl.
  *F04B 43/00*    (2006.01)
  *F04B 43/08*    (2006.01)
  (Continued)

(52) U.S. Cl.
  CPC ..... *F04B 43/0081* (2013.01); *A61M 5/14228* (2013.01); *F04B 43/082* (2013.01);
  (Continued)

(58) Field of Classification Search
  CPC ...... F04B 43/082; F04B 43/113; F04B 39/00; F04B 43/12; F04B 43/08; F04B 45/06; F04B 45/08; F04B 49/02; F04B 49/10; F04B 53/22; F04B 2207/70; A61M 5/14244; A61M 5/16854; A61M 5/1413;
  (Continued)

(56) References Cited

U.S. PATENT DOCUMENTS

| 4,155,362 A | * | 5/1979 | Jess | ............... | A61M 5/14228 |
| | | | | | 128/DIG. 12 |
| 4,493,706 A | * | 1/1985 | Borsanyi | ........... | A61M 5/142 |
| | | | | | 128/DIG. 12 |

(Continued)

FOREIGN PATENT DOCUMENTS

| EP | 2197515 | 6/2010 |
| WO | 0238204 | 5/2002 |

(Continued)

OTHER PUBLICATIONS

European Office Action from corresponding European Patent Application No. 14742107.7, dated Oct. 5, 2017.

*Primary Examiner* — Charles Freay
(74) *Attorney, Agent, or Firm* — Greer, Burns & Crain, Ltd.

(57) ABSTRACT

An infusion pump for transferring fluid through tubing of an administration set connected to the pump, where the pump includes a housing and a pumping mechanism mounted to the housing. The pumping mechanism includes a plurality of pumping fingers, a motor for sequentially, reciprocally moving the plurality of pumping fingers, and an occlusion sensor configured to detect reverse loading of the tubing to the pumping mechanism. In operation, the occlusion sensor causes at least one of a triggering of an alarm and prevention of the operation of the pumping mechanism when the sensor detects that the administration set tubing is reverse loaded to the pumping mechanism.

4 Claims, 4 Drawing Sheets

(51) Int. Cl.
*A61M 5/142* (2006.01)
*A61M 5/168* (2006.01)

(52) U.S. Cl.
CPC ............. *A61M 2005/16863* (2013.01); *A61M 2205/276* (2013.01)

(58) Field of Classification Search
CPC .... A61M 5/14228; A61M 2005/16863; A61M 2005/16868; A61M 2005/16872; Y10T 436/106664; A61B 17/1628; A61B 2019/4868; A61B 17/1624; A61B 17/1626; A61B 2017/00367
USPC ... 417/477.4, 477.7, 479, 476, 477.3, 477.1; 604/67, 151, 500; 310/244, 242
See application file for complete search history.

(56) References Cited

U.S. PATENT DOCUMENTS

| | | | | |
|---|---|---|---|---|
| 5,018,945 A * | 5/1991 | D'Silva | ............. | A61M 5/14228 417/12 |
| 5,217,355 A * | 6/1993 | Hyman | ............. | A61M 5/14228 417/474 |
| 5,584,667 A * | 12/1996 | Davis | ................... | A61M 5/142 417/474 |
| 5,695,473 A * | 12/1997 | Olsen | ................ | A61M 5/16859 128/DIG. 13 |
| 5,827,223 A * | 10/1998 | Butterfield | ........ | A61M 5/16859 604/65 |
| 6,164,921 A * | 12/2000 | Moubayed | ........ | A61M 5/14228 251/7 |
| 6,371,732 B1 * | 4/2002 | Moubayed | ........ | A61M 5/14228 417/44.1 |
| 6,572,604 B1 * | 6/2003 | Platt | ................. | A61M 5/16854 604/500 |
| 7,892,199 B2 | 2/2011 | Mhatre et al. | | |
| 8,029,253 B2 * | 10/2011 | Rotem | .............. | A61M 5/14228 417/478 |
| 8,353,864 B2 | 1/2013 | Davis | | |
| 2003/0214412 A1 * | 11/2003 | Ho | ..................... | A61M 5/14228 340/611 |
| 2003/0236489 A1 * | 12/2003 | Jacobson | .......... | A61M 5/16886 604/67 |
| 2005/0047946 A1 * | 3/2005 | Davis | ................... | B41J 2/17596 417/477.11 |
| 2005/0069425 A1 * | 3/2005 | Gray | ................. | A61M 5/14224 417/392 |
| 2005/0145008 A1 | 7/2005 | Vanderveen et al. | | |
| 2010/0179131 A1 * | 7/2010 | Klein | .................... | A61K 31/473 514/217.11 |
| 2011/0060284 A1 * | 3/2011 | Harr | .................. | A61M 5/14244 604/153 |
| 2011/0300010 A1 * | 12/2011 | Jarnagin | ............ | A61B 17/3207 417/477.2 |
| 2011/0318198 A1 * | 12/2011 | Johnson | ................ | A61M 5/168 417/300 |
| 2012/0257986 A1 * | 10/2012 | Momeni | .................. | F04B 43/12 417/53 |
| 2013/0030345 A1 * | 1/2013 | Gronau | ............... | F04B 43/1253 604/6.01 |
| 2013/0204174 A1 * | 8/2013 | Olde | ................... | A61M 1/3653 604/6.11 |
| 2013/0253420 A1 * | 9/2013 | Favreau | ................. | F04B 49/10 604/67 |
| 2013/0280104 A1 * | 10/2013 | Heide | .................... | F04B 43/12 417/53 |

FOREIGN PATENT DOCUMENTS

| | | |
|---|---|---|
| WO | 20090137645 | 11/2009 |
| WO | 2012/144219 A1 | 10/2012 |
| WO | 20130057109 | 4/2013 |

* cited by examiner

INFUSION PUMP INCLUDING REVERSE LOADING PROTECTION

FIELD OF THE INVENTION

The present invention relates to a system for protecting against misloading of an infusion system, and more particularly, to a system including misloading protection features that enable the proper connection of an administration set to an infusion pump.

BACKGROUND

Infusion systems deliver fluids, including nutrients and medications, to a patient. Such systems include pumps programmed to supply these fluids to patients in predetermined dosages and at designated time intervals. Errors in administration of the fluids through an infusion system can result from many causes including misloading or misconnection of an administration set to the system. These issues can lead to over or under infusion of the fluids to the patient, missed treatments or delayed treatments that can significantly affect a patient's health and recovery. As a result, guidelines have been established to enhance the safety of infusion systems.

There are several safety checks that clinicians typically perform such as "line management" or "line tracing" to help eliminate misconnections or misloading. Setting up such infusion systems and detailed connection management procedures imposes a time burden on the clinician and is prone to errors, particularly as the complexity of a patient's overall infusion system increases. That is, the multiple administrations sets, medications, junctions, access ports, pump channels in infusion systems, increases the amount of time required to perform infusion system safety checks and also introduces additional opportunities for error.

Accordingly, there is a need for a system that facilitates proper connection of an administration set to an infusion system while reducing human error.

SUMMARY

The present infusion pump includes misloading protection features that guide the proper connection of an administration set to an infusion pump while helping to minimize human error.

In an embodiment, an infusion pump for transferring fluid through tubing of an administration set is provided where the pump includes a housing and a pumping mechanism mounted to the housing. The pumping mechanism includes a plurality of pumping fingers, a motor for sequentially, reciprocally moving the plurality of pumping fingers, and an occlusion sensor configured to detect reverse loading of the tubing to the pumping mechanism. The occlusion sensor causes the motor to turn off when the occlusion sensor detects the reverse loading of the tubing to the pumping mechanism.

DETAILED DESCRIPTION

Figure 1:
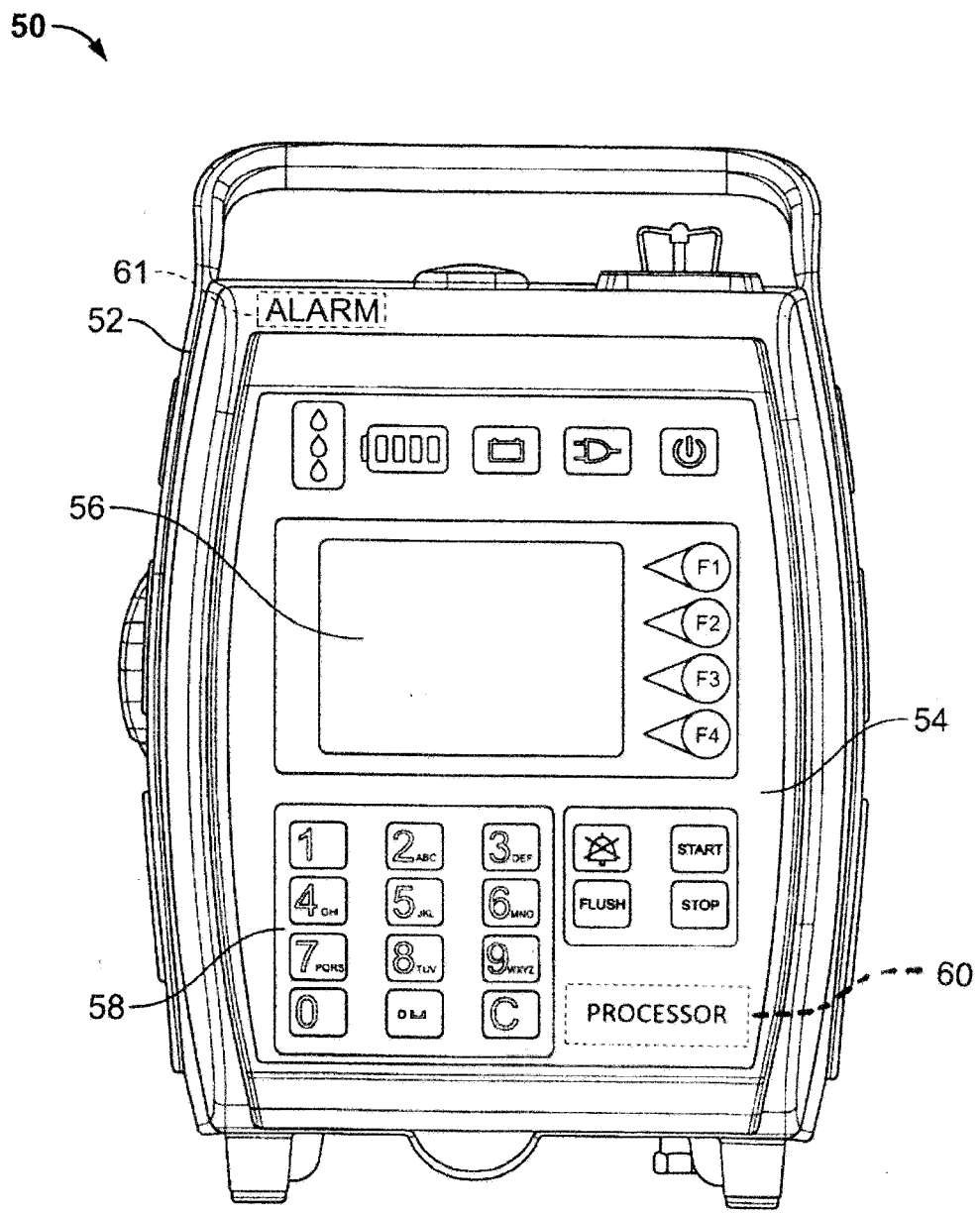
FIG. 1 is a perspective view showing an infusion pump according to an embodiment of the present invention.

Referring to FIGS. 1-5, an infusion delivery system including an infusion pump 50 is used to deliver fluids, such as medications or nutrients, to a patient in predetermined quantities and at periodic time intervals. The infusion pump 50 may be a small portable pump or a larger pump, such as the infusion pump disclosed in U.S. Pat. No. 5,018,945, which is incorporated herein by reference. As shown in FIG. 1, the infusion pump 50 includes a housing 52, a door 54 pivotally connected to the housing and a display 56 and a keypad 58, among other inputs, on the door. The display 56 and the keypad 58 are used to program the infusion pump, and more specifically, a processor 60 in the pump to set the fluid delivery amount and time interval, which in turn, is communicated to pumping mechanism 62.

Figure 3:
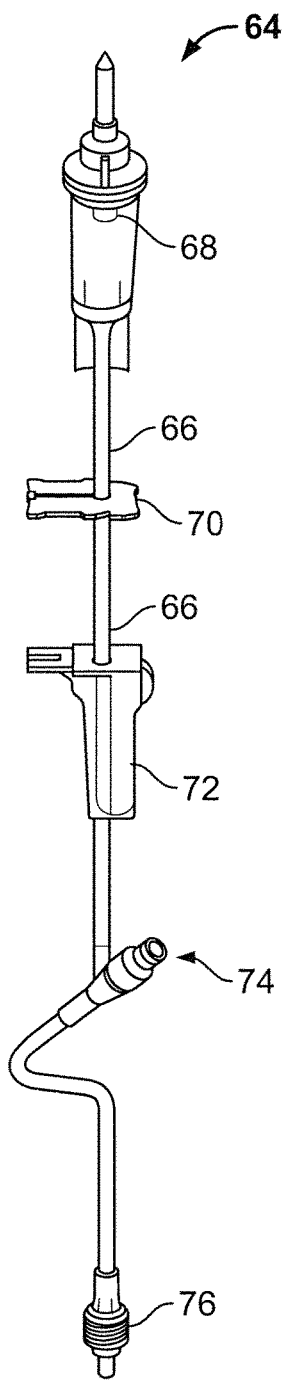
FIG. 3 is a perspective view showing an embodiment of an administration set that is connected to the infusion pump of FIG. 1.

Fluids move to and from the infusion pump 50 through a fluid administration set 64 shown in FIG. 3. The administration set 64 is attached to the pump 50 by routing a portion of the tubing 66 of the administration set 64 between the door 54 and the housing 52. Preferably, the administration set 64 includes a drip chamber 68 directly connected to a fluid container (not shown), such as an intravenous fluid bag, a slide clamp 70 used to clamp a portion of the tubing 66 and control the flow of the fluid through the tubing, a roller clamp 72 also used to control the flow of the fluid, a Y-site connector 74 and a luer lock or luer slip 76 at an end of the administration set 64 where the luer lock is connected to a needle inserted in a patient for delivering the fluid to the patient. A portion of the administration set tubing 66, and more specifically, the portion of the tubing 66 between the slide clamp 70 and the roller clamp 72, is inserted in channels 78 defined by the housing 52 and positioned over the pumping mechanism 62. As described below, the pumping mechanism 62 includes a series of reciprocating pumping fingers 80 that contact the tubing 66 for controlling the amount of the fluid delivered to the patient.

Figure 4:
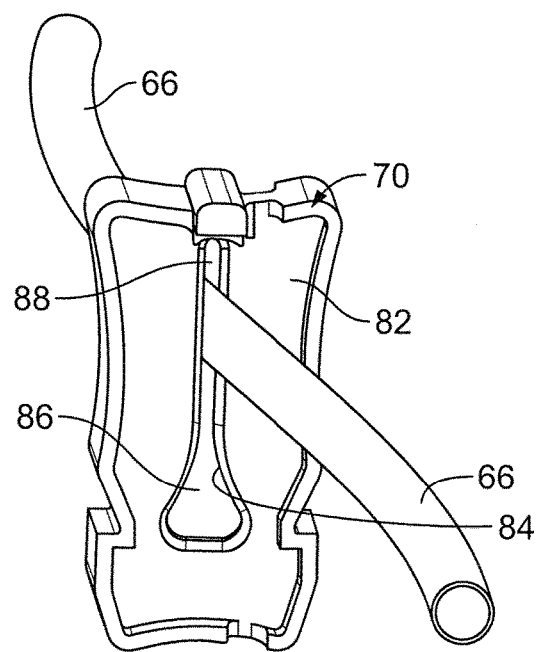
FIG. 4 is a fragmentary, perspective view showing tubing of the administration set of FIG. 3 inserted through and clamped by a slide clamp of the infusion pump of FIG. 1.

During administration of a fluid to a patient, it is critical to prevent free flow of the fluid to the patient. Free flow occurs when a fluid is allowed to flow unrestricted to the patient resulting in too much of the fluid to be supplied to the patient, i.e., an over infusion. To help prevent free flow of the fluid through the administration set 64, the slide clamp 70 is attached to the tubing 66 of the administration set. As shown in FIG. 4, the slide clamp 70 includes a body 82 having a central opening 84 with a wide portion 86 and a narrow portion 88. The tubing 66 is moved into the narrow portion 88 of the slide clamp opening 84 to clamp or crimp the tubing and prevent free flow of the fluid through the tubing. This is particularly critical when the administration set 64 is being inserted in or otherwise attached to the infusion pump 50 to deliver a fluid to the patient.

Figure 5:
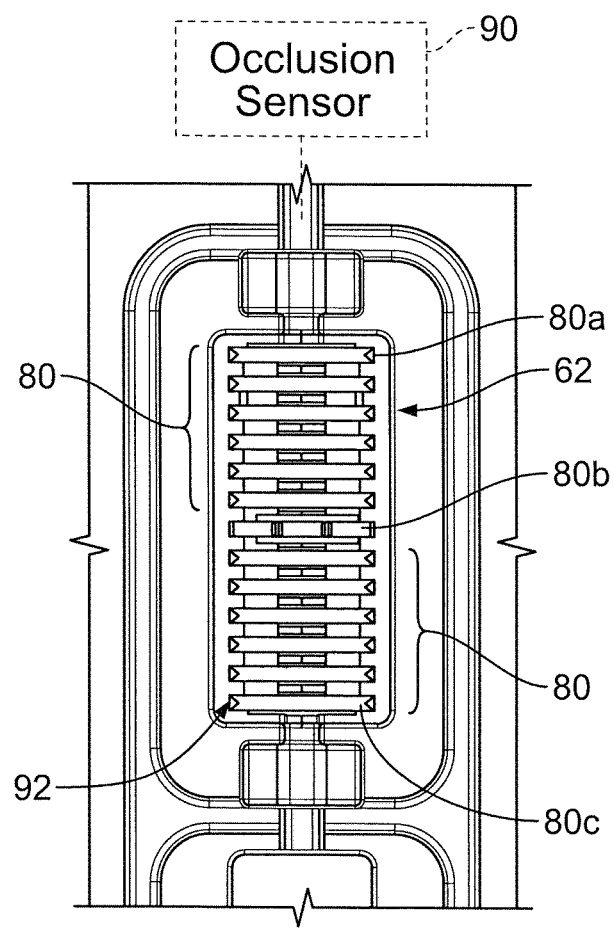
FIG. 5 is a fragmentary, front view of an embodiment of a pumping mechanism associated with the infusion pump of FIG. 1, where the pumping mechanism includes an occlusion sensor and a valve.

Referring now to FIG. 5, another issue that results from the set up of the infusion pump 50 is a reverse loading condition where the administration set 64 is connected to the infusion pump so that the fluid flow is in a reverse or opposite direction to the desired fluid flow direction, i.e., from the fluid container to the patient. With reverse loading, the fluid flows from the patient to the fluid container thereby posing a health risk to the patient. To overcome reverse loading, an embodiment of the present infusion pump 50 includes an occlusion sensor or pressure sensor 90 associated with the pumping mechanism 62 and a valve 92 associated with pumping finger 80c of the pumping fingers 80.

Figure 2:
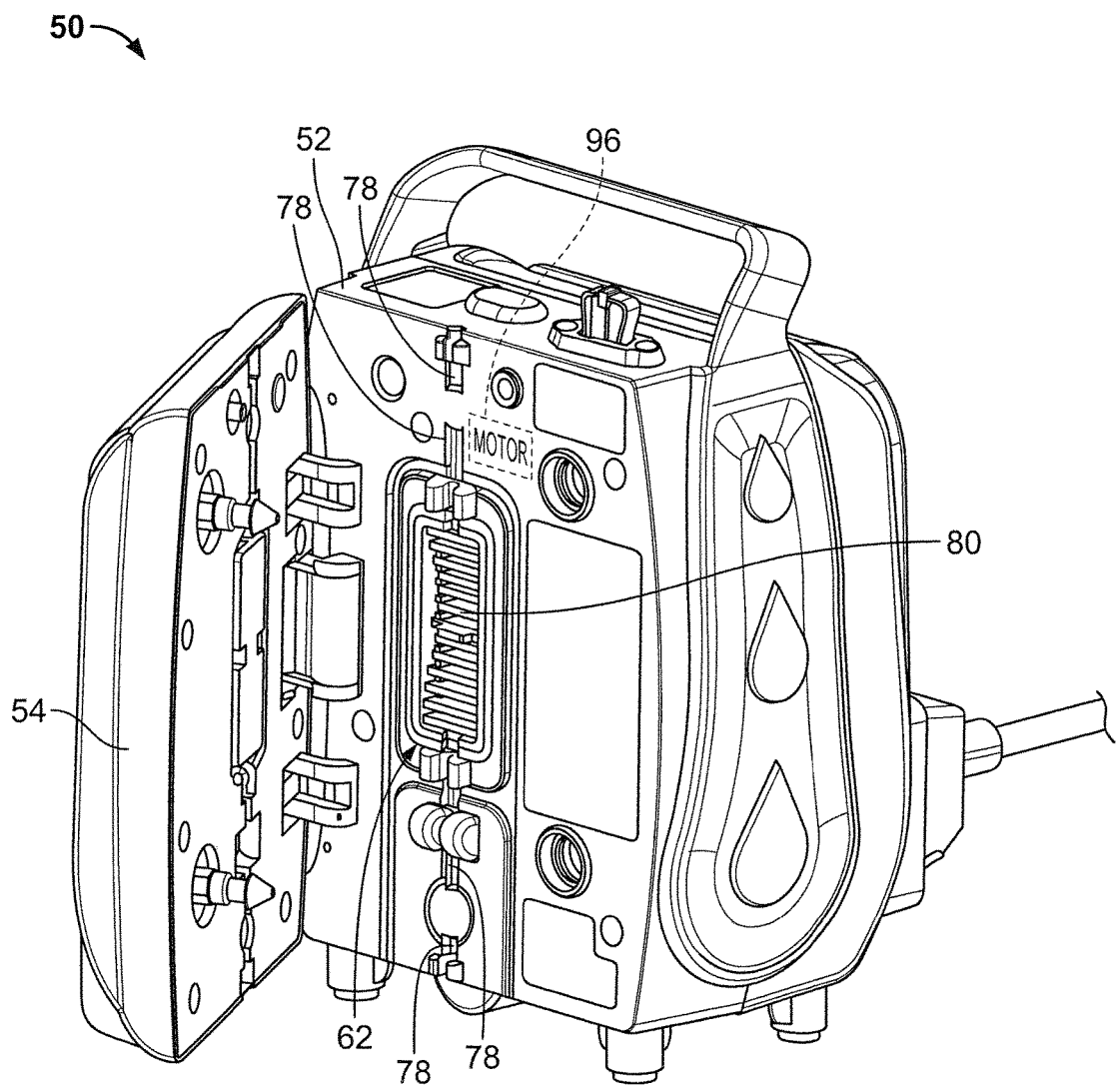
FIG. 2 is a perspective view showing the infusion pump of FIG. 1 where the door is in the open position.

In the illustrated embodiment, the administration set is connected to the infusion pump 50 so that the slide clamp 70 is open while the roller clamp 72 is closed. A tube misload sensor 80b performs an initial check to detect and determine if the tubing 66 of the administration set is misloaded on the pumping mechanism as described above. If the tubing 66 is loaded properly, a designated rate, preferably a high flow rate, such as 999 milliliters per hour (mL/hr), is programmed into the processor 60 of the infusion pump 50 to allow quick pressure build up in the pumping mechanism 62 to minimize sensor detection time. Also, the valve 92 occludes or blocks the flow of fluid through the tubing 66 adjacent to pumping finger 80c. Next, the processor 60 sends a signal to the pumping fingers 80 to run quickly through a pumping sequence from pumping finger 80a to pumping finger 80c. When there is normal loading of the administration set 64 to the infusion pump 50, the occlusion sensor 90 detects a downstream occlusion at pumping finger 80c. Alternatively, if there is reverse loading of the administration set 64, i.e., the roller clamp 72 is linked to the top side of the pumping mechanism 62 (connected to the tubing prior to pumping finger 80a), the occlusion sensor 90 detects an upstream occlusion due to the roller clamp 72. Since the signals associated with normal loading and reverse loading of the administration set 64 are different, the occlusion sensor 90 is able to detect when the administration set 64 is reverse loaded. After the initial loading check, if the administration set 64 is properly or normally loaded, the motor 96 does a short reverse run, i.e., the pumping finger sequence goes from pumping finger 80c to pumping finger 80a, to avoid a bolus to the patient. A start key on the keypad 58 of the infusion pump 50 is then pressed which causes the valve 92 associated with pumping finger 80c to unocclude the tubing 66 of the administration set 64 and allow normal infusion or flow of the fluid. If reverse loading of the administration set 64 to the infusion pump 50 is detected by the occlusion sensor 90, the occlusion sensor sends a signal to the processor 60, which in turn, triggers an alarm 61 (FIG. 1), such as an audio indicator, a visual indicator, a tactile indicator or any combination of these indicators or cues, to alert a user that the administration set is reverse loaded. It should be appreciated that any suitable alarms or indicators may be used to alert the user. The processor 60 may also prevent operation of the infusion pump 50 when reverse loading is detected by the occlusion sensor 90. For example, the processor 60 may deactivate or shut off the pumping mechanism motor 96 (FIG. 2).

In another embodiment, the administration set 64 is loaded or connected to the infusion pump 50 where both the slide clamp 70 and the roller clamp 72 are opened or in an open position. Similar to the embodiment above, the tube misload sensor 80b determines if the tubing 66 of the administration set 64 has been misloaded on the pumping mechanism 62. If the tubing 66 is loaded properly, a designated flow rate, and preferably a high flow rate, such as a flow rate of 999 milliliters per hour (mL/hr), is set or programmed into the processor 60 to allow quick pressure build up in the pumping mechanism 62 to minimize sensor detection time. The pumping mechanism 62 then does a short reverse run where the pumping finger sequence goes from pumping finger 80c to pumping finger 80a and is held for a short period of time and then released. As described above, there are two possible loading conditions, normal loading and reverse loading. With normal loading, the administration set tubing 66 positioned between pumping finger 80a and pumping finger 80c is refilled with the fluid. With reverse loading, the tubing 66 between pumping finger 80a and pumping finger 80c is not refilled with the fluid. In this regard, the misload sensor 80b is able to detect force or pressure. Therefore, since the signals associated with normal loading and misloading are different, the sensor 80b can also detect when the administration set 64 is normally loaded or reverse loaded and trigger an alarm or other suitable indicator as described above if reverse loading is detected. It should be appreciated that the misload sensor 80b is preferably a highly pressure sensitive sensor to detect the force/pressure difference between normal loading and misloading of the administration set 64.

The present infusion pump 50 includes misloading protection features that help prevent free reverse loading of an administration set to the pump. The protection features of the present infusion pump enable users to properly set up of the infusion pump and deliver fluid to a patient while minimizing human error.

While the principles of the present infusion pump have been described above in connection with specific apparatus and applications, it is to be understood that this description is made only by way of example and not as a limitation on the scope of the claims following below.

What is claimed is:

1. An infusion pump for transferring fluid through tubing of an administration set connected to the pump, the pump comprising:
   a housing including a processor;
   a pumping mechanism mounted to said housing, said pumping mechanism including a plurality of pumping fingers, a motor for sequentially, reciprocally moving said plurality of pumping fingers;
   a valve mounted to said housing and associated with one of said plurality of pumping fingers, said valve being in communication with said processor and configured to occlude the tubing at a point adjacent to said one of said plurality of pumping fingers, and
   an occlusion sensor mounted to said housing and associated with one of said plurality of pumping fingers, said processor being in communication with said motor, said valve, and said occlusion sensor and being configured to detect a blockage in an upstream portion of the tubing, which is upstream of the plurality of pumping fingers on a first side of the pumping mechanism wherein the tubing extends from a fluid container to the pumping mechanism, or a downstream portion of the tubing, which is downstream of the plurality of pumping fingers on a second side of the pumping mechanism wherein the tubing extends from the pumping mechanism to a patient, wherein reverse loading of the tubing to the pumping mechanism causes a blockage in the upstream portion of the tubing; and
   wherein said processor causes at least one of a triggering of an alarm and prevention of the operation of said pumping mechanism when said occlusion sensor detects a blockage in the upstream portion of the tubing mounted on the pumping mechanism.

2. The pump of claim 1, further comprising a misload sensor configured to detect when the tubing is loaded into channels associated with the pumping mechanism.

3. The pump of claim 1, wherein said alarm includes one of an audio indicator, a visual indicator or a tactile indicator.

4. An infusion pump for transferring fluid through tubing of an administration set connected to the pump, the pump consisting of:
   a housing including a processor; and
   a pumping mechanism mounted to said housing, said pumping mechanism including a plurality of independently movable pumping fingers, a motor for sequentially, reciprocally moving said plurality of pumping fingers, and an occlusion sensor mounted to said housing and associated with said pumping mechanism, said processor being in communication with said motor, one of said plurality of independently movable pumping fingers and said occlusion sensor and being configured to detect a blockage in an upstream portion of the tubing, which is upstream of the plurality of pumping fingers on a first side of the pumping mechanism wherein the tubing extends from a fluid container to the pumping mechanism, or a downstream portion of the tubing, which is downstream of the plurality of pumping fingers on a second side of the pumping mechanism wherein the tubing extends from the pumping mechanism to a patient, wherein reverse loading of the tubing to the pumping mechanism causes a blockage in the upstream portion of the tubing,
   wherein said processor causes at least one of a triggering of an alarm and prevention of the operation of said pumping mechanism when said occlusion sensor detects a blockage in the upstream portion of the tubing mounted on the pumping mechanism.

\* \* \* \* \*